(12) United States Patent
Varley et al.

(10) Patent No.: US 11,737,897 B2
(45) Date of Patent: Aug. 29, 2023

(54) PROSTHESIS ELECTRODE

(71) Applicant: COVVI Limited, Harrogate (GB)

(72) Inventors: Edward William Varley, Leeds (GB); Robert Spares, Bradford (GB)

(73) Assignee: COVVI LIMITED, Harrogate (GB)

( * ) Notice: Subject to any disclaimer, the term of this patent is extended or adjusted under 35 U.S.C. 154(b) by 138 days.

(21) Appl. No.: 17/045,677

(22) PCT Filed: Apr. 3, 2019

(86) PCT No.: PCT/GB2019/050956
§ 371 (c)(1),
(2) Date: Oct. 6, 2020

(87) PCT Pub. No.: WO2019/197801
PCT Pub. Date: Oct. 17, 2019

(65) Prior Publication Data
US 2021/0022890 A1 Jan. 28, 2021

(30) Foreign Application Priority Data
Apr. 12, 2018 (GB) ...................................... 1806043

(51) Int. Cl.
*A61F 2/72* (2006.01)
*A61F 2/80* (2006.01)
*A61B 5/296* (2021.01)
*A61B 5/00* (2006.01)

(52) U.S. Cl.
CPC .................. *A61F 2/72* (2013.01); *A61F 2/80* (2013.01); *A61B 5/296* (2021.01); *A61B 5/6811* (2013.01); *A61B 2560/0468* (2013.01)

(58) Field of Classification Search
CPC ..... A61F 2/72; A61F 2/76; A61F 2/80; A61B 5/296; A61B 5/6811; A61B 2560/0468
See application file for complete search history.

(56) References Cited

U.S. PATENT DOCUMENTS

| | | | |
|---|---|---|---|
| 8,747,485 B1 * | 6/2014 | Nunez | A61F 2/6607 623/49 |
| 2007/0265711 A1 * | 11/2007 | Klein | A61F 2/7812 623/33 |
| 2021/0370060 A1 * | 12/2021 | Koppe | A61F 2/68 |

FOREIGN PATENT DOCUMENTS

| | | | | |
|---|---|---|---|---|
| DE | 202006007460 U1 | 9/2007 | | |
| DE | 102011015502 B3 * | 9/2012 | ........... | A61F 2/7812 |
| EP | 2620127 A1 * | 7/2013 | ........... | A61B 5/0492 |
| EP | 2620127 A1 | 7/2013 | | |

(Continued)

OTHER PUBLICATIONS

Losier, Yves, et al. "An overview of the UNB hand system." Myoelectric Symposium, 2011. (Year: 2011).*

(Continued)

*Primary Examiner* — Christie Bahena
(74) *Attorney, Agent, or Firm* — Alston & Bird LLP

(57) ABSTRACT

The present application describes apparatus (100) for locating an electrode unit on a prosthesis socket, comprising an electrode unit (102) locatable in a socket aperture (106) and having a first abutment surface (118) for engagement with an inner surface (120) of the socket; and a retaining element (104) locatable on the electrode unit and having a further abutment surface (126) for engagement with an outer surface (128) of the socket or the first abutment surface of the electrode unit.

19 Claims, 3 Drawing Sheets

(56) References Cited

FOREIGN PATENT DOCUMENTS

GB        2173569 A  * 10/1986  ............... A61F 2/76
GB        1806043.4     10/2018

OTHER PUBLICATIONS

Ottobock, Electrode 13E200—Instructions for Use, 2011 (Year: 2011).*
Steeper. Electrode Fabrication Guide. Steeper Website. (Year: 2022).*
International Preliminary Examining Authority, International Preliminary Report on Patentability Under Chapter I for International Application No. PCT/GB2019/050956, dated Oct. 13, 2020, (10 pages), Geneva, Switzerland.
International Searching Authority, International Search Report and Written Opinion for International Application No. PCT/GB2019/050956, dated Sep. 4, 2019, (15 pages), Rijswijk, Netherlands.

* cited by examiner

PROSTHESIS ELECTRODE

CROSS REFERENCE TO RELATED APPLICATIONS

This application is a National Stage Application, filed under 35 U.S.C. § 371, of International Application No. PCT/GB2019/050956, filed Apr. 3, 2019, which international application claims priority to and the benefit of United Kingdom Application No. 1806043.4, filed Apr. 12, 2018; the contents of both of which as are hereby incorporated by reference in their entireties.

BACKGROUND

Related Field

The present invention relates to securely mounting an electrode unit in a prosthetic socket. In particular, but not exclusively, the present invention relates to a myoelectric electrode unit, retaining element, and an assembly for securely mounting the electrode unit in a socket of a prosthesis.

Description of Related Art

A conventional prosthetic hand is typically controlled by two electrodes located on a user's residual limb which detect electrical signals generated by the user's muscles and send corresponding signals to a controller of the prosthetic hand. The controller actuates motors to selectively move the fingers and thumb of the hand in response to the received signals.

Some conventional myoelectric electrodes are mounted in a flexible grommet which itself is mounted in an aperture of the socket. The grommet is required to seal the interface between the aperture wall and the electrode. However, the electrode is often permanently fixed in the grommet and both components are often relatively complex, time consuming, and costly to manufacture. Another conventional method of mounting an electrode in a socket aperture is via suspension mounting which consists of a pair of flexible mounting pins extending in opposite directions from the electrode casing. The pins engage in corresponding recesses provided on the socket such that the electrode is suspended in the aperture. However, these recesses are complex, time consuming, and costly to provide on a socket. Furthermore, the interface between the electrode and the socket wall is not sealed which is undesirable for sockets which are retained on a user's residual limb by way of a vacuum.

BRIEF SUMMARY

It is an aim of certain embodiments of the present invention to provide an assembly for securely and efficiently mounting an electrode to a prosthesis socket.

It is an aim of certain embodiments of the present invention to provide an electrode mounting assembly that allows a user to easily install an electrode in a socket, and to remove the same from the socket if desired.

It is an aim of certain embodiments of the present invention to provide an assembly for mounting an electrode in a sealed and/or suspended manner with respect to a socket.

It is an aim of certain embodiments of the present invention to provide an electrode mounting assembly that is relatively non-complex to manufacture and which requires the socket to have a non-complex aperture therein with relatively low tolerances.

According to a first aspect of the present invention there is provided apparatus for locating an electrode unit on a prosthesis socket, comprising:

an electrode unit locatable in a socket aperture and having a first abutment surface for engagement with an inner surface of the socket; and a retaining element locatable on the electrode unit and having a further abutment surface for engagement with an outer surface of the socket or the first abutment surface of the electrode unit.

Optionally, the first abutment surface is provided by an outwardly extending flange portion of the electrode unit.

Optionally, the flange portion is substantially resilient.

Optionally, the electrode unit comprises at least one first connecting region for interlocking engagement with at least one further connecting region of the retaining element.

Optionally, the first connecting region comprises one of a projection and recess and the further connecting region comprises the other of a projection and recess.

Optionally, the first and further connecting regions comprise interlocking teeth.

Optionally, the at least one first connecting region comprises a first connecting region on each of opposed first sides of the electrode unit for interlocking engagement with corresponding further connecting regions of the retaining element.

Optionally, the at least one first connecting region comprises a first connecting region on each of opposed further sides of the electrode unit for interlocking engagement with corresponding further connecting regions of the retaining element.

Optionally, the retaining element comprises a wall portion defining a through aperture for receiving the electrode unit and the at least one further connecting region is disposed on an inner surface of the wall portion.

Optionally, the retaining element further comprises a flange portion extending outwardly from the wall portion to provide the further abutment surface.

Optionally, the wall portion provides the further abutment surface.

Optionally, the retaining element further comprises a pair of projections extending outwardly in opposed directions from the wall portion.

Optionally, each projection comprises a resilient pin.

According to a second aspect of the present invention there is provided a prosthesis comprising apparatus according to the first aspect of the present invention and a socket for receiving a residual limb.

According to a third aspect of the present invention there is provided an electrode unit for a prosthesis socket, comprising:

an electrode body locatable in a socket aperture and having an abutment surface for engagement with an inner surface of the socket.

Optionally, the abutment surface is provided by a flange portion extending outwardly from the electrode body.

Optionally, the flange portion is substantially resilient.

Optionally, the electrode unit comprises at least one connecting region for interlocking engagement with at least one corresponding connecting region of a retaining element locatable on an electrode unit to retain the electrode unit with respect to a socket.

Optionally, the at least one connecting region comprises a set of teeth disposed on each of opposed outer surfaces of the electrode body.

According to a fourth aspect of the present invention there is provided a retaining element for retaining an electrode unit on a prosthesis socket, comprising:
- a wall portion defining a through aperture for receiving an electrode unit; and
- an abutment surface for engagement with an outer surface of a socket or an abutment surface of the electrode unit.

Optionally, at least one connecting region is disposed on an inner surface of the wall portion for interlocking engagement with at least one corresponding connecting region of an electrode unit to retain the electrode unit with respect to a socket.

Optionally, the at least one connecting region comprises a set of teeth disposed on each of opposed inner surfaces of the wall portion.

Optionally, the retaining element further comprises a flange portion extending outwardly from the wall portion to provide the abutment surface.

Optionally, the wall portion provides the further abutment surface.

Optionally, the retaining element further comprises a pair of projections extending outwardly in opposed directions from the wall portion.

Optionally, each projection comprises a resilient pin.

According to a fifth aspect of the present invention there is provided a method of locating an electrode unit on a prosthesis socket, comprising:
- locating an electrode unit in an aperture of a prosthesis socket such that a first abutment surface of the electrode unit engages with an inner surface of the socket; and
- locating a retaining element on the electrode unit such that a further abutment surface of the retaining element engages with an outer surface of the socket or the first abutment surface of the electrode unit.

Optionally, the method comprises:
- by at least one first connecting region of the electrode unit and at least one corresponding further connecting region of the retaining element, interlocking the retaining element on the electrode unit.

Optionally, the method comprises:
- clamping the socket between the first abutment surface and the further abutment surface.

Optionally, the method comprises:
- mounting the retaining element in a pair of opposed recesses disposed on or in a wall of the socket.

BRIEF DESCRIPTION OF THE FIGURES

Certain embodiments of the present invention will now be described with reference to the accompanying drawings in which.

DETAILED DESCRIPTION OF VARIOUS EMBODIMENTS

Figure 1:
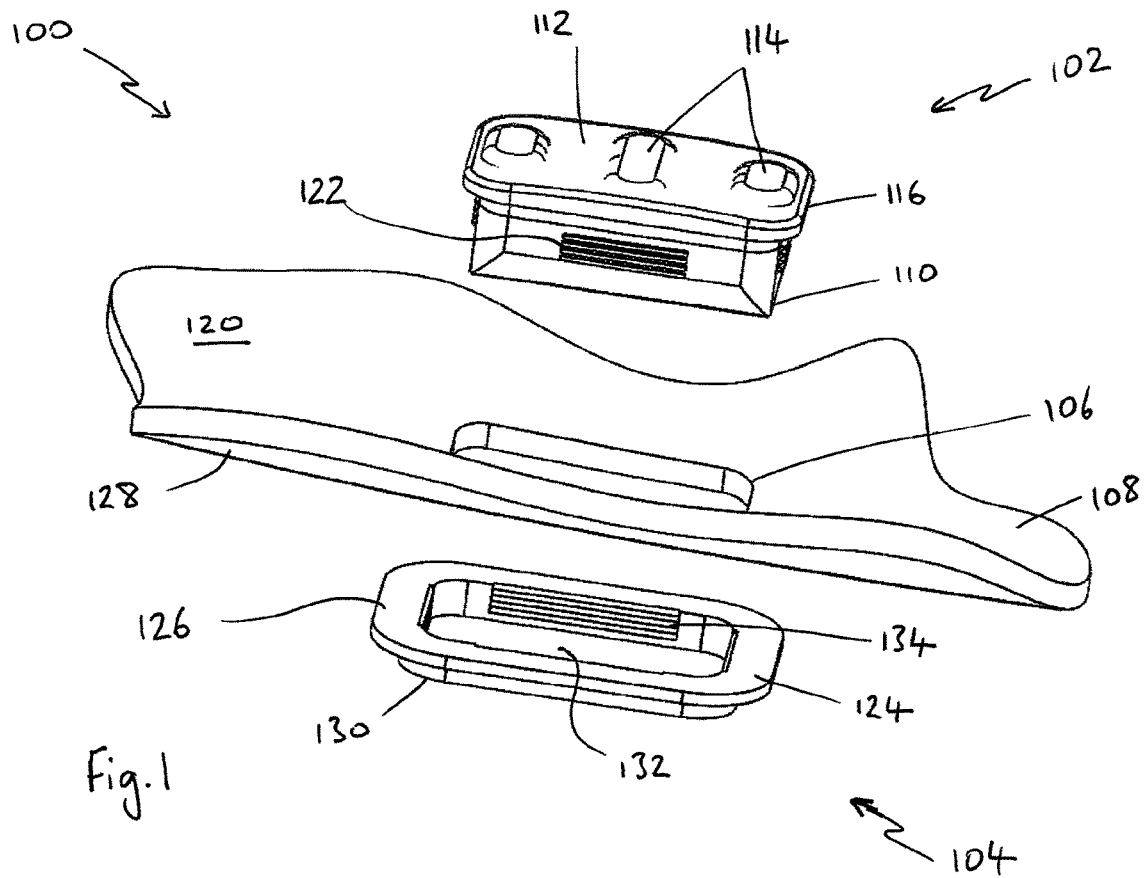
FIG. 1 illustrates an electrode mounting assembly according to a first embodiment of the present invention in a disassembled state.
Figure 2:
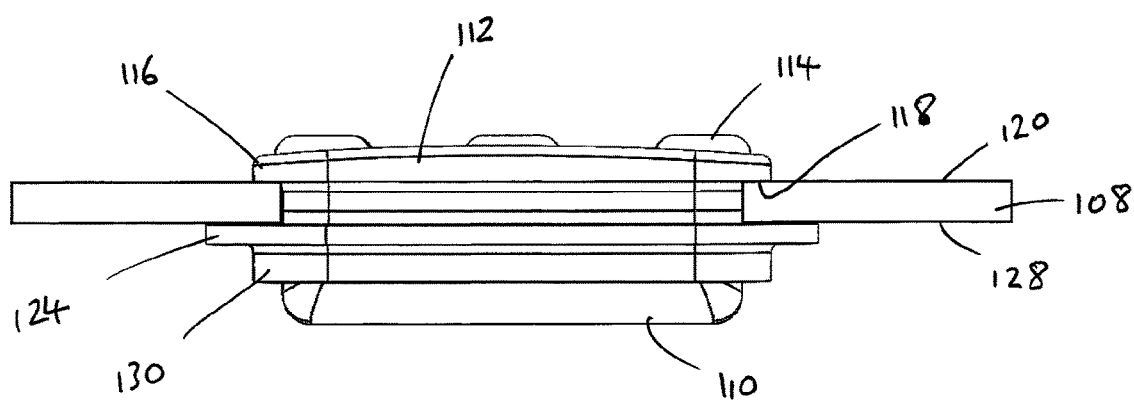
FIG. 2 illustrates the assembly of FIG. 1 in an assembled state wherein the electrode is securely mounted to a socket in a sealed manner.

As illustrated in FIGS. 1 and 2, an electrode assembly 100 according to certain embodiments of the present invention includes an electrode unit 102, such as a myoelectrical electrode unit or the like, and a retaining element 104 for securely retaining the electrode 102 in an aperture 106 of a socket 108 of an upper limb prosthesis. The aperture 106 is substantially rectangular but could be any suitable shape such as square, circular, oval or the like, to receive a correspondingly shaped electrode. The thickness of the socket wall is around 2 to 3 mm.

The electrode unit 102 includes an electrode body having a lower body portion 110 for housing suitable electronics and an upper body portion 112 for locating a set of spaced apart sensors 114 for contacting the skin of a user's residual limb received in the socket 108 in use. The sensors may be biocompatible titanium skin contact sensors or the like. The dimensions of the electrode unit are around 30×20×10 mm. The upper body portion 112 of the electrode extends beyond the side surfaces of the lower body portion 110 to thereby provide a flange 116 around an upper region of the electrode. An abutment surface 118 of the flange 116 engages with an inner surface 120 of the socket 108 when the electrode 102 is mounted thereto in use. The upper body portion 112 is a substantially flexible yet resilient material, such as Thermoplastic Elastomer (TPE), Thermoplastic Urethane (TPU), silicone, rubber, or the like, to efficiently seal the interface between the flange 116 and the socket 108 in use. The lower body portion 110 of the electrode is a substantially rigid material such as a hardened plastic, Polyamide (pa6), Actel (pom), PolyEtherEtherKetone (PEEK), Polybutylene terephthalate (PBT), or the like. The upper and lower body portions 110, 112 may be moulded separately and joined by a suitable joining technique, or formed integrally, to provide a sealed unit. Each of the four outer surfaces of the lower portion 110 of the electrode body includes a set of elongate and parallel projections in the form of teeth 122 extending outwardly therefrom. The length and thickness of each tooth 122 is around 12 mm and 0.8 mm respectively and each set has around four teeth. The teeth are oriented substantially parallel with the flange 116. The teeth may however be any suitable number, shape and size to provide an interlocking engagement.

The retaining element 104 includes a continuous flange 124 providing an abutment surface 126 for engagement with an outer surface 128 of the socket 108 in use. The retaining element 104 further includes a continuous wall 130 extending substantially perpendicularly from the flange in a direction away from the abutment surface 126 or socket 108 in use. The wall 130, and in turn the flange 124 extending therefrom, define an aperture 132 for receiving the lower portion 110 of the electrode 102 in use. The aperture 132 is substantially rectangular but may be any suitable shape and size to correspond with the lower portion 110 of the electrode 102. The retaining element 104 is a substantially rigid material such as a hardened plastic, Polyamide (pa6), Actel (pom), PolyEtherEtherKetone (PEEK), Polybutylene terephthalate (PBT), or the like. Alternatively, at least the flange 124 may be substantially flexible/resilient to conform with the shape of the socket and efficiently seal the interface therebetween if desired. As shown in FIG. 1, each inner surface of the wall 130 includes a set of elongate and parallel projections in the form of teeth 134 extending inwardly therefrom. The length and thickness of each tooth 134 corresponds to the teeth 122 of the electrode body and respective sets of teeth 134, 122 are configured to interlock with each other to securely mount and retain the electrode 102 in the socket aperture 106.

In use, the lower portion 110 of the electrode 102 is located in the socket aperture 106 from an inner side of the socket 108. The flexible upper portion 112 of the electrode conforms with the profile of the inner surface 120 of the socket and seals the interface therebetween. The retaining element 104 is then pushed on to the lower portion 110 of the electrode from an outer side of the socket 108 such that the respective sets of latching teeth 122, 134 of the retaining element and electrode interlock to securely and efficiently clamp the socket wall between the abutment surface 118 of the electrode flange 116 and the abutment surface 126 of the retaining element flange 124, as illustrated in FIG. 2. The retaining element flange 124 provides a secure and stable clamping surface to prevent the electrode moving in use and to provide an efficient sealing force.

In an alternative embodiment, the retaining element flange 124 may not be required and an upper surface of the wall 130 abuts with the outer surface 128 of the socket 108. Further alternatively, the wall 130 of the retaining element 104 may not be present and the flange 124 may have sufficient depth for providing a latching element/s, e.g. teeth 134, for interlocking with a corresponding latching element/s, e.g. teeth 122, of the electrode 102. Furthermore, the flange and/or wall may be continuous or intermittent.

The sets of teeth 122, 134 may be other forms of latching element to securely clamp the electrode onto the socket, such as at least one projection on one of the electrode and retaining element and at least one recess on the other. Likewise, one of the electrode and retaining element may have at least one projection or recess and the other may have a plurality of projections and recesses to provide a number of selectable indexed positions for the electrode to engage with the retaining element responsive to a thickness of the socket wall. For example, the electrode 102 may for example have a set of elongate teeth on at least two opposed sides and the retaining element 104 may have one tooth on opposed inner surfaces to correspond with the teeth of the electrode to thereby provide a number of different positions for the retaining element to interlock with the electrode depending on the thickness of the socket and/or flexibility of the electrode flange 116 for efficient sealing with the socket 108. The retaining mechanism may aptly provide a snap-fit or ratchet connection, or the like, and may provide a fixed or releasable connection. For example, the retaining element 104 may have teeth 134 on a first pair of opposed inner surfaces and may be flexible yet resilient to allow the other pair of opposed surfaces to be squeezed towards each other such that the first pair of opposed surfaces move outwardly from each other and the teeth disengage from the electrode teeth to thereby allow the retaining element 104 to be removed from the electrode 102. This type of releasable connection may be desirable for removing the electrode from the socket when the latter requires cleaning.

Figure 5:
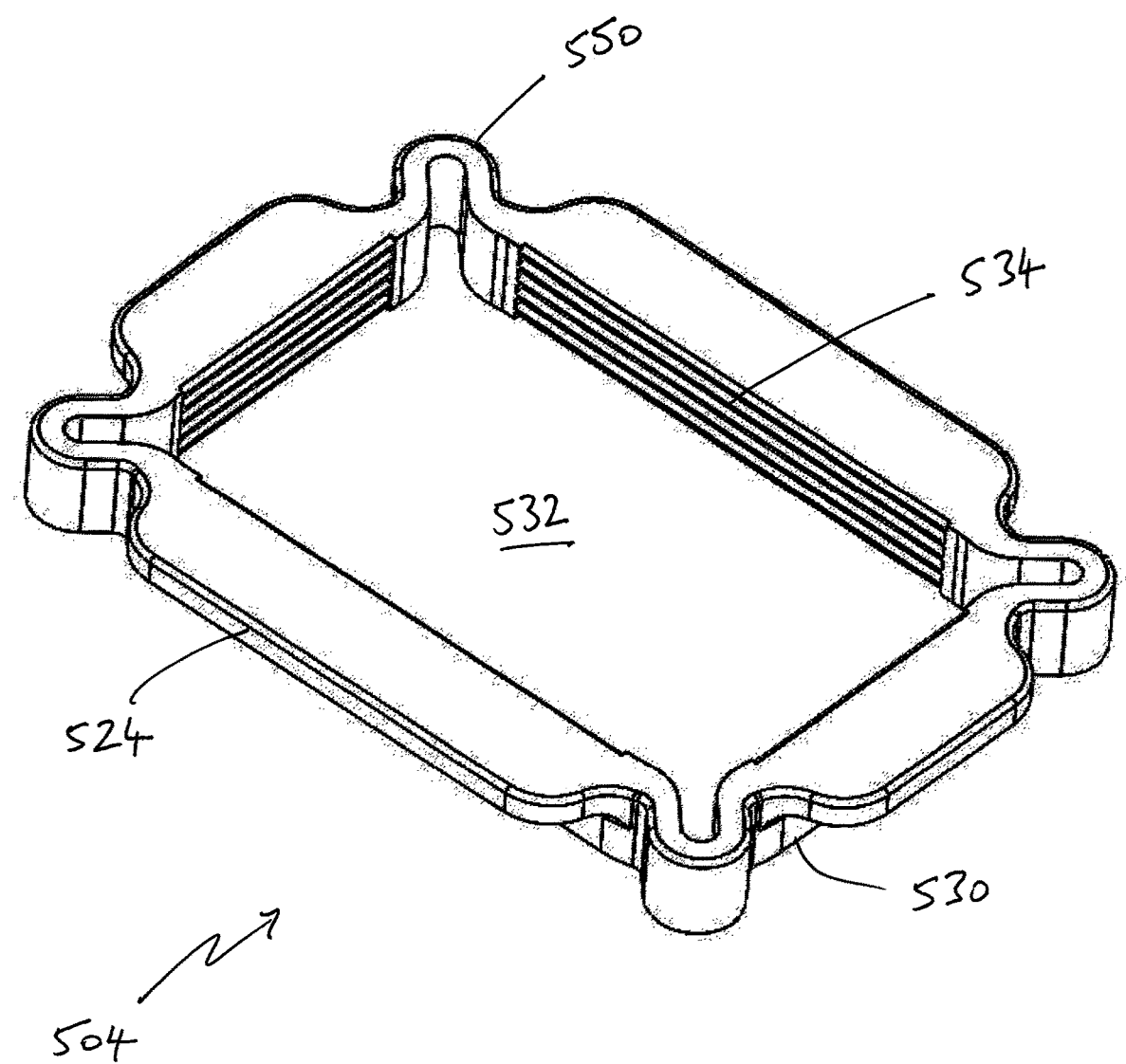
FIG. 5 illustrates a further embodiment of a retaining element according to certain embodiments of the present invention.

A further embodiment of a retaining element 504 according to certain embodiments of the present invention is illustrated in FIG. 5. The retaining element 504 includes a continuous wall portion 530 defining a substantially rectangular aperture 532 for receiving an electrode unit 102 according to certain embodiments of the present invention. Each of the four main inner surfaces of the wall portion 530 include a set of teeth 534 for interlocking engagement with the corresponding teeth 122 of the electrode unit. Each corner region 550 of the wall portion 530 is U-shaped in plan cross section to thereby provide a hinge point outboard of the inner surfaces and allow the same to move relative to each other. The flange 524 is intermittent in that is consists of four spaced apart flange portions each extending substantially perpendicularly from a respective side of the wall portion 530. The spaced apart flange portions 524 also allow the wall portions to move relative to each other. In other words, the retaining element 504 is substantially flexible in a lateral direction relative to a direction in which the retaining element 504 is located on to the electrode unit 102. This allows the retaining element to expand when being located on an electrode unit and to accommodate any tolerances or misalignments between the two components. Such flexibility may also allow the retaining element to be removable from the electrode unit if desired, such as for cleaning purposes or the like.

Figure 3:
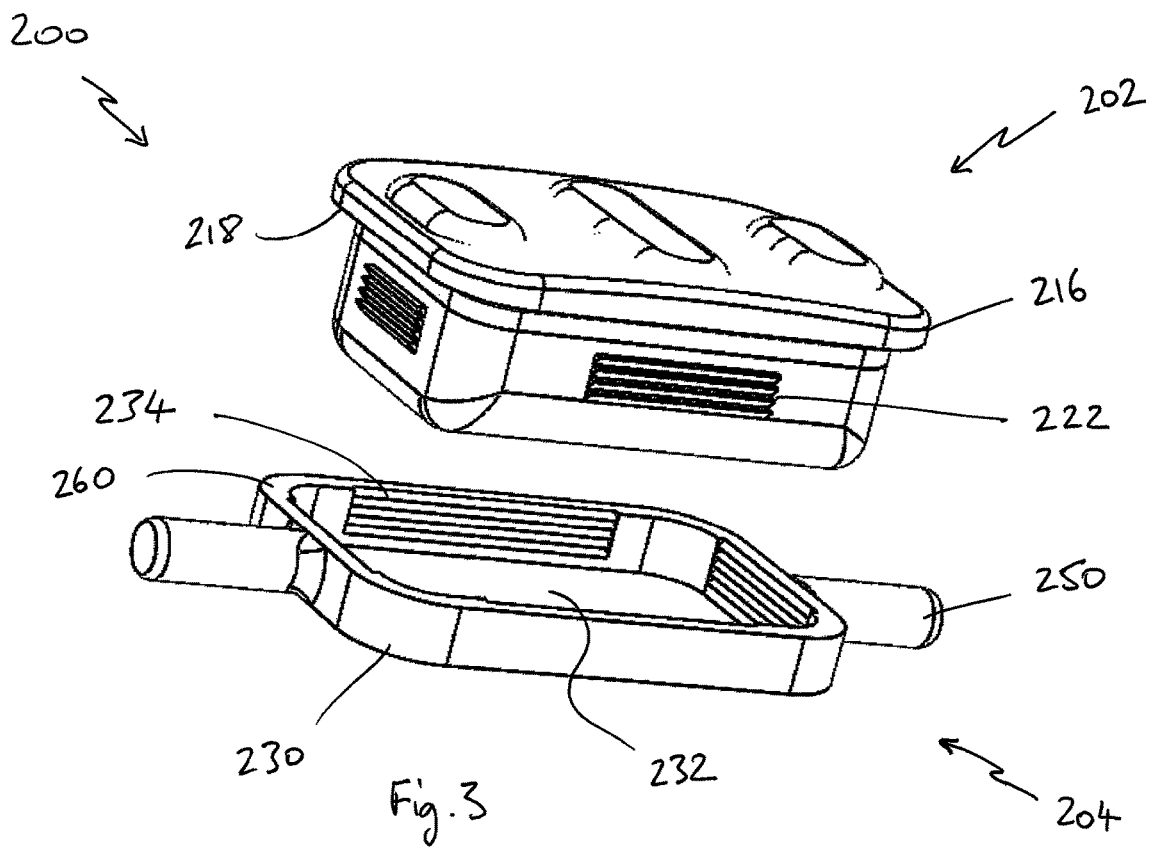
FIG. 3 illustrates an electrode mounting assembly according to a further embodiment of the present invention in a disassembled state.
Figure 4:
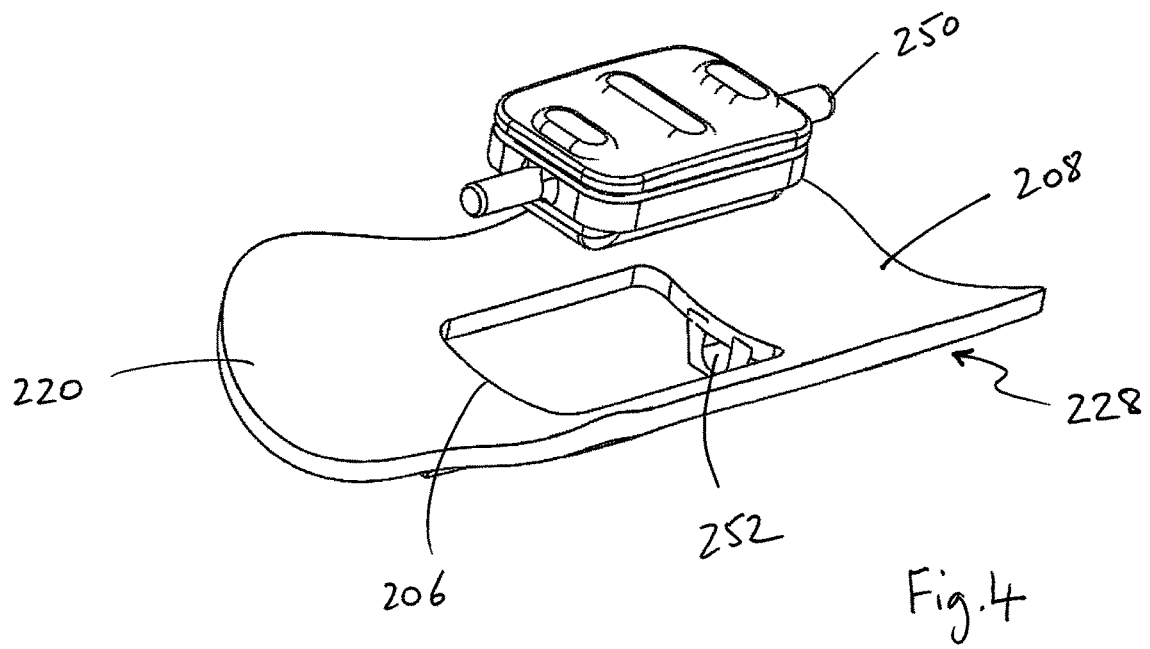
FIG. 4 illustrates the assembly of FIG. 3 in an assembled state for mounting to a socket in a suspended manner.

A further electrode assembly 200 according to certain embodiments of the present invention is illustrated in FIGS. 3 and 4. In this assembly, the retaining element 204 comprises a wall portion 230 defining a substantially rectangular through aperture 232 and includes a set of teeth 234 on each inner surface of the wall. The teeth 234 are configured to engage and interlock with corresponding teeth 222 of the electrode 202 to thereby locate the electrode in the retaining element 204 and with respect to the socket 208.

The retaining element 204 further includes a pair of flexible pins 250 each extending outwardly in opposite directions from a respective one of opposed outer surfaces of the wall portion 230. The outer surfaces are the shorter surfaces of the rectangular wall and pins 250 are located on the longitudinal axis of the retaining element 204. The pins 250 are rubber but may be any suitable flexible yet resilient material to allow the same to be located in corresponding mounting apertures 252 provided on the outer surface 228 of the socket 208, as illustrated in FIG. 4, and securely suspend the electrode 202 with respect to the socket 208. The flange 216 of the electrode is sized and shaped such that its lower abutment surface 218 engages with the upper surface 260 of the retaining element 204 to provide additional support for the electrode when suspended in the retaining element. The socket aperture 206 may also be sized and shaped to correspond with the outer profile of the wall portion 230 of the retaining element 204 to closely receive the same and prevent any lateral translational and/or rotational movement of the retaining element and electrode in the socket aperture, whilst allowing the same to float inwardly and outwardly to accommodate any muscle movement and/or expansion/contraction of a user's limb in the socket.

Aptly, the flange 216 of the electrode may be sized to engage with the inner surface 220 of the socket 208 and the pins 250 may be configured by way of material, construction and/or shape to urge the electrode 204 outwardly relative to the inner surface 220 of the socket such that the flange 216 is urged against the inner surface 220 of the socket to provide a clamping force and effective seal if desired between the flange 216 and the socket 208. As shown in FIG. 4, the mounting apertures 252 are bonded to, or formed on, the outer surface 228 of the socket 208 but may be provided in the wall of the socket aperture 206 if the thickness of the socket is sufficient. Each mounting aperture 252 may be substantially elongate to receive a respective one of the elongate pins 250 or each pin may be a relatively small projection and each mounting aperture may be a correspondingly sized recess or indent to receive a respective one of the projections in a snap-fit arrangement.

Certain embodiments of the present invention therefore provide apparatus in the form of an assembly for securely and efficiently mounting a myoelectric electrode to a prosthesis socket. The assembly allows a user to easily install an electrode in a socket and remove the same from the socket for cleaning if required. The assembly in accordance with certain embodiments of the present invention may be used to mount the electrode in a sealed and/or suspended manner with respect to a socket. The assembly is relatively non-complex to manufacture and the socket itself only requires an aperture therein with relatively low tolerances.

The invention claimed is:

1. An assembly for mounting an electrode unit to a prosthesis socket, the assembly comprising:
   a monolithic electrode unit locatable in a socket aperture provided in a socket wall of a prosthesis socket, the electrode unit comprising:
   an upper body portion having at least one sensor for contacting a user's limb received in the socket in use and providing a first abutment surface for engagement with an inner surface of the socket wall when the electrode unit is located in the socket aperture;
   and a lower body portion locatable through the socket aperture and comprising a first pair of opposed outer surfaces each including a plurality of elongate and parallel projections extending at least partially along a length of each of the first pair of opposed outer surfaces and outwardly therefrom to define a first set of teeth;
   and a retaining element directly locatable on the lower body portion of the electrode unit and providing a second abutment surface for engagement with an outer surface of the socket wall, wherein:
   the retaining element comprises a wall portion defining a through aperture for receiving the lower body portion;
   and a first pair of opposed inner surfaces of the wall portion each include a plurality of elongate and parallel projections extending at least partially along a length of each of the first pair of opposed inner surfaces and inwardly therefrom to define a second set of teeth for interlocking connection with the first set of teeth when the retaining element is pushed on to the lower body portion of the electrode unit in a direction perpendicular to a length of the first and second sets of teeth.

2. The assembly according to claim 1, wherein the first abutment surface is provided by an outwardly extending flange portion of the upper body portion of the electrode unit.

3. The assembly according to claim 2, wherein the flange portion is substantially resilient.

4. The assembly according to claim 1, wherein an opposed second pair of the outer surfaces of the lower body portion of the electrode unit each include a plurality of elongate and parallel projections extending outwardly therefrom to define a third set of teeth for interlocking connection with a fourth set of teeth defined by a plurality of elongate and parallel projections extending inwardly from a second pair of opposed inner surfaces of the wall portion of the retaining element.

5. The assembly according to claim 1, wherein the retaining element further comprises a flange portion extending outwardly from the wall portion of the retaining element to provide the second abutment surface.

6. The assembly according to claim 1, wherein the wall portion of the retaining element provides the second abutment surface.

7. The assembly according to claim 6, wherein the retaining element further comprises a pair of projections extending outwardly in opposed directions from the wall portion of the retaining element.

8. The assembly according to claim 7, wherein each projection comprises a resilient pin.

9. A prosthesis comprising the assembly according to claim 1 and a socket for receiving a residual limb.

10. The assembly according to claim 1, wherein:
    the first pair of opposed outer surfaces are substantially planar surfaces; and
    the first pair of opposed inner surfaces are substantially planar surfaces.

11. The assembly according to claim 1, wherein:
    the first pair of opposed outer surfaces are substantially parallel relative to one another; and
    the first pair of opposed inner surfaces are substantially parallel relative to one another.

12. The assembly according to claim 1, wherein at least one of:
    the plurality of elongate and parallel projections of the first pair of opposed outer surfaces extend along less than a length of each of the first pair of opposed outer surfaces; or
    the plurality of elongate and parallel projections of the first pair of opposed inner surfaces extend along less than a length of each of the first pair of opposed inner surfaces.

13. The assembly according to claim 1, wherein:
    the first set of teeth extend along less than a length of each of the first pair of opposed outer surfaces; and
    the second set of teeth extend along less than a length of each of the first pair of opposed inner surfaces.

14. A monolithic electrode unit locatable in a socket aperture provided in a socket wall of a prosthesis socket, the electrode unit comprising:
    an upper body portion having at least one sensor for contacting a user's limb received in the socket in use and providing a first abutment surface for engagement with an inner surface of the socket wall when the electrode unit is located in the socket aperture;
    and a lower body portion locatable through the socket aperture and comprising a first pair of opposed outer surfaces each including a plurality of elongate and parallel projections extending at least partially along a length of each of the first pair of opposed outer surfaces and outwardly therefrom to define a first set of teeth for interlocking connection with a second set of teeth defined by a plurality of elongate and parallel projections extending at least partially along a length of and inwardly from a first pair of opposed inner surfaces of a retaining element directly locatable on the lower body portion of the electrode unit and providing a second abutment surface for engagement with an outer surface of the socket wall when the retaining element is pushed on to the lower body portion of the electrode unit in a direction perpendicular to a length of the first and second sets of teeth.

15. The electrode unit according to claim 14, wherein the first abutment surface is provided by an outwardly extending flange portion of the upper body portion.

16. The electrode unit according to claim 15, wherein the flange portion is substantially resilient.

17. A method of locating an electrode unit in a socket aperture provided in a socket wall of a prosthesis socket, the method comprising:

locating a lower body portion of a monolithic electrode unit through a socket aperture providing in a socket wall of a prosthesis socket such that a first abutment surface of an upper body portion of the electrode unit engages with an inner surface of the socket, wherein the upper body portion comprises at least one sensor for contacting a user's limb received in the socket in use and the lower body portion comprises a first pair of opposed outer surfaces each including a plurality of elongate and parallel projections extending at least partially along a length of each of the first pair of opposed outer surfaces and outwardly therefrom to define a first set of teeth;

locating a retaining element directly on the lower body portion of the electrode unit, wherein the retaining element comprises a second abutment surface and a first pair of opposed inner surfaces each including a plurality of elongate and parallel projections extending at least partially along a length of each of the first pair of opposed inner surfaces and inwardly therefrom to define a second set of teeth;

interlockingly connecting the first set of teeth with the second set of teeth by pushing the retaining element onto the lower body portion of the electrode unit in a direction perpendicular to a length of the first and second sets of teeth;

and engaging the second abutment surface of the retaining element with an outer surface of the socket or the first abutment surface of the electrode unit.

18. The method according to claim 17, comprising:
clamping the socket wall between the first abutment surface and the second abutment surface.

19. The method according to claim 17, comprising:
mounting a pair of projections each extending outwardly in opposed directions from the wall portion of the retaining element in a pair of opposed and respective recesses disposed on or in the socket wall.

* * * * *